United States Patent [19]

Herman et al.

[11] 4,090,394
[45] May 23, 1978

[54] PLASTIC BOTTLE TESTING

[75] Inventors: James N. Herman; David M. Kaczorowski, both of Toledo, Ohio

[73] Assignee: Owens-Illinois, Inc., Toledo, Ohio

[21] Appl. No.: 738,516

[22] Filed: Nov. 3, 1976

[51] Int. Cl.$^2$ .............................................. G01M 3/02
[52] U.S. Cl. ........................................ 73/37; 73/49.4
[58] Field of Search .................. 73/37, 37.5, 49.2, 89, 73/49.4, 97, 149

[56] References Cited

U.S. PATENT DOCUMENTS

| | | | |
|---|---|---|---|
| 2,967,427 | 1/1961 | LeBlanc | 73/149 |
| 3,230,760 | 1/1966 | Fryer, Jr. et al. | 73/37 |
| 3,555,881 | 1/1971 | Ayers | 73/37 |
| 3,580,050 | 5/1971 | Waldron | 73/37 |
| 3,916,673 | 11/1975 | Gass et al. | 73/37 |
| 3,955,402 | 5/1976 | Harvill | 73/37 |

*Primary Examiner*—Richard C. Queisser
*Assistant Examiner*—Joseph W. Roskos
*Attorney, Agent, or Firm*—Charles S. Lynch; E. J. Holler

[57] ABSTRACT

Method and apparatus are provided for producing a stress-strain type curve for evaluating the functionality of a thermoplastic bottle. The method generally comprises the steps of internally pressurizing a thermoplastic bottle with an incompressible fluid by relative movement of a piston and a cylinder, sensing the pressure of said fluid and sensing the relative movement of said piston and cylinder as said bottle is being pressurized by such movement, and graphically and automatically recording said sensed pressure and said sensed relative movement as said bottle is being pressurized. The technique is rapidly performed with high sensitivity and automatically produces a curve in which one axis is pressure related and another axis is relatable to the deformation of the bottle.

8 Claims, 1 Drawing Figure

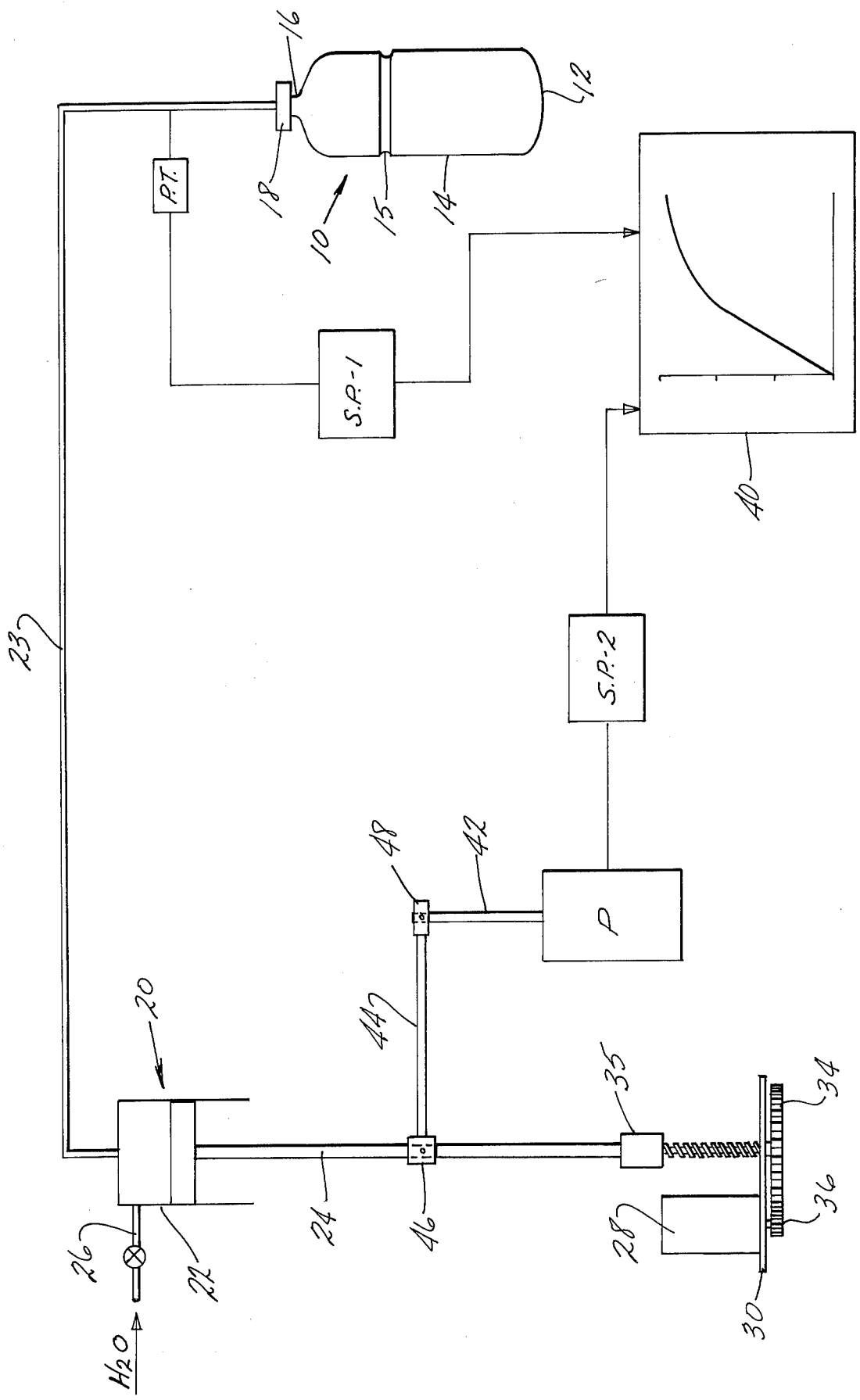

PLASTIC BOTTLE TESTING

THE INVENTION

The present invention relates to measuring and testing and, more particularly, the invention relates to testing with fluid pressure, namely, an incompressible fluid, like water. Even yet more particularly the present invention relates to testing with hydrostatic pressure and automatically developing a stress-strain type curve for a thermoplastic bottle.

The prior art is well aware of methods and apparatus for testing the internal pressure, or bursting, strength of glass bottles by pressurizing the bottle with an incompressible fluid. Exemplary of such teachings is U.S. Pat. No. 3,955,402. Additionally an apparatus is available from American Glass Research, Inc. of Butler, Pennsylvania which is described as an increment pressure tester for the fluid pressure testing of glass bottles. One such suitable commercially available instrument is the Model 1200s Increment Pressure Tester. Generally this pressure tester employs a piston which is moved to increase water pressure within the bottle. Such testers generate, electronically, a pressure program by shunting a strain gage pressure transducer with a series of calibrated resistors. A stepping switch is employed which advances one position every three seconds, or so, introducing a new resistance representing the next higher pressure level. The transducer continuously monitors the test pressure in the system and compares it to the desired pressure level; any difference signal is amplified and used to drive a servomotor which moves the pressure piston to reduce this difference to zero. The pressure is increased in these units be employing a servomotor which drives the piston through a gear and ball screw linear activator and the test is automatically terminated when a preset upper pressure limit is reached or when a glass bottle fails by bursting. For fuller particulars reference may be had to the brochure of American Glass Research, Inc. entitled "Increment Pressure Tester Model 1200s," which is hereby incorporated by reference.

Relatively recently a great deal of interest has developed in producing biaxially oriented thermoplastic bottles having barrier properties and strength characteristics which make them conducive for use in the packaging of carbonated beverages for example, soft drinks and beer. Such containers, which are receiving wide testing and evaluation, include containers made from the so-called high barrier nitriles, i.e. interpolymers formed from acrylonitrile and/or methacrylonitrile, wherein the content of the acrylonitrile and/or methacrylonitrile is typically in excess of about 60% by weight, and also bottles made from linear saturated polyesters, especially polymers which are produced by the interpolymerization of ethylene glycol and terephthalic acid, i.e., poly(ethylene terephthalate). It will be readily apparent that the functionality of such containers, and especially the biaxially oriented containers, i.e., the ability of these containers to function over long periods of time in their intended environment, are affected by numerous factors; these factors, in turn, affect the deformation of the bottle which is an extremely important characteristic. That is, even a small volumetric expansion of a carbonated beverage thermoplastic bottle, for example, an expansion on the order of less than 5% will cause the carbonation to migrate from the beverage to the bottle head space and results in a deterioration of the product due to lowered carbonation. Thus the resistance to deformation is an extremely important characteristic of such bottles. Factors which influence the resistance of the bottle to deformation include the polymer employed, its strength and modulus (stiffness), side wall thickness, the uniformity of material distribution throughout the bottle, bottle design, and the fabrication conditions by which the bottle had been formed including, for example, how well the bottle was biaxially oriented during fabrication. Heretofore the functionality of the thermoplastic bottles had been evaluated by testing methods which required extremely long periods of time to produce the needed information. It will be readily apparent that in the process of developing thermoplastic bottles having the needed functionality such prolonged testing is entirely unacceptable when it is desired to evaluate various materials, bottle thickness, fabrication techniques, and the like. Additionally, in commercial operation it will be readily apparent that such prolonged testing is unacceptable.

Thus it will be readily apparent that there is a need in the art for providing a rapid and sensitive method to allow one to measure the functionality of thermoplatic bottles and especially, for example, biaxially oriented thermoplastic bottles. The above-indicated glass pressure testing methods and apparatus have been used for plastic bottles but are not satisfactory for this purpose because they provide inadequate information for purposes of evaluating the functionality of thermoplastic bottles.

In accordance with the present invention this need in the art for providing a rapid and sensitive measuring technique for evaluating the functionality of a thermoplastic bottle is satisfied by employing fluid pressure testers of the type indicated above and by attaching certain appendages thereto whereby a stress-strain type curve is automatically plotted in short periods of time, i.e., on the order of several seconds to 1 or 2 minutes during the testing procedure.

Thus in accordance with this invention there is provided a testing method for evaluating the functionality of thermoplastic bottles, i.e., bottles typically having a nominal capacity of about 64 ozs. and less, and more typically 32 ozs. and less, which method comprises driving a piston so as to increase the internal pressure of an incompressible fluid within a thermoplatic bottle, and automatically graphically recording the movement of said driven piston and the pressure of fluid in said bottle as the internal pressure is increased by the movement of said driven piston.

In accordance with another feature of this invention there is provided an apparatus for testing the functionality of a thermoplastic bottle comprising a piston and cylinder assembly in sealed fluid communication with said bottle, means for driving said piston so as to increase the internal pressure of said fluid in said bottle, means responsive to the movement of said piston for generating a piston-position related electrical signal, means for providing a bottle-pressure related electrical signal and, means operatively receiving said signals and graphically presenting said signals in the form of a graph in which one axis is pressure related and another axis is related to the piston position.

As indicated the test is performed in a very short order of time, for example on the order of several seconds to a minute or two, and a stress-strain type curve is autmotically produced which is indicative of bottle functionality. The stress-strain type curve is a graphic presentation in which one axis is related to the internal pressure and the other axis is related to the position or movement of the piston which is employed to increase the internal pressure in the thermoplastic bottle. As will be apparent since a piston and cylinder assembly is employed the linear displacement of the piston can be related to a volume displacement of water which in turn is related to the deformation of the bottle. Such stress-strain type curves, by an evaluation of their initial slope, the elastic yield point, the general curve shape, and specific pressures, provide invaluable, rapidly and sensitively produced information which allows one to measure the functionality of the container and especially its stiffness, resistance to deformation, overall strength, and quality. This testing method is well adapted for quality control testing, it can be employed to predict the long term functionality of the container and has been used successfully more than one year prior to the filing of the application to optimally design parison configurations to produce an optimized thermoplastic biaxially oriented container.

U.S. Pat. No. 3,580,050 relates to fluid pressure testing of fabrics, not bottles, wherein a liquid from a reservoir chamber is pumped into another chamber containing the fabric and a piston float type device monitors the level change from the chamber and is graphically presented by the use of a marking device which is attached to the rod of the piston float. A pressure axis is plotted by mechanically moving the recording device either by use of a hydraulic air pressure transmitter or by use of a pressure transducer which in turn drives a motor to move the recording device. U.S. Pat. No. 3,230,760 relates to the non-destructive testing of pressure vessels, for example gas storage cylinders, reactor tanks, pressure tubing and pipes, pipelines, tank cars, storage tanks, boilers, boiler tubes, and missile parts wherein water is pumped from a liquid supply container to the test vessel; by means of a pressure transducer and a weight transducer a plot of pressure and water weight pumped is obtained. U.S. Pat. No. 3,916,673 discloses the testing of elastically and plastically deformable pipelines and employs a pump to supply an incompressible fluid to the pipeline. A graphic representation is produced by employing a pressure transducer as the monitor, or sensing means, for pressure and the volume of water employed is measured by means of a turbine flowmeter which in turn is graphically presented. These patents, however, have no recognition of the present inventive concept. For example the use of pumps and turbine flowmeters are ill-suited to the present application wherein small thermoplastic bottles are employed and wherein the total deformation of the bottle is typically on the order of 15 ml or less. Thus, for example, it will be seen that the sensitivity for testing thermoplastic bottles are lacking in such patents.

The attached drawing schematically illustrates a preferred embodiment of the present invention as described hereinafter.

The simple nature and other advantageous features of the present invention will become more apparent by reference to the attached drawing. In the drawing there is shown a thermoplastic bottle, for example a biaxially-oriented poly(ethylene terephthalate) bottle 10 which generally includes a bottom wall portion 12, a circumferential wall 14, and a neck portion 16. These bottles are well known and are adapted to be inserted into a stabilizing base and generally also include a grip facilitating recess 15 in wall 14. Typically in operation this bottle will first be filled with water and then the bottle will be sealingly attached to a sealing head 18. There is also provided a piston-cylinder assembly generally designated 20 which includes a cylinder 22 and a piston with an integral piston rod 24. Conduit 23 is in sealed fluid communication with the head space of the cylinder and with the sealing head 18 which in turn establishes sealed fluid communication with the internal portion of bottle 10. Also in fluid communication with the head space of cylinder 22 is a valved conduit 26 allowing for the insertion of water into the conduit 23 and head space of cylinder 22. Thus in operation after the water filled bottle 10 is inserted and sealed to the sealing head 18 the valve of the valve conduit 26 is opened to fill conduit 23 and the head space of cylinder 22 with water after which time the valve is closed and the test begun.

Associated with piston rod 24 are suitable means for moving same upwardly to thereby increase the internal pressure in bottle 10 as the test proceeds. Such means are exemplified by a servomotor 28 carried by a suitable supporting member 30. The rotatable shaft 32 of motor 28 passes through the support 30 and serves to drive main gear 34 through intermediate gear 36. Of course gear 34 is rotatably mounted to support 30 by a suitable bearing assembly (not shown) such as a New Departure bearing No. Z 99501. Affixed to gear 34 for rotation therewith is a drive screw 38 which is operatively connected, generally at its upper portion, to piston rod 24 so that upon rotation of the drive screw 38, by rotation of gear 34, piston rod 24 is driven, or moved, upwardly to increase the pressure in bottle 10. One suitable means of establishing such an operative connection is to employ a Saginaw ball screw linear activator 35. An ideal arrangement, as described above, is to employ the previously indicated Increment Pressure Tester of American Glass Research, Inc., namely their model 1200s. This assembly generally includes a somewhat elongate piston-cylinder assembly 20 in which the internal diameter of the cylinder is quite small, i.e., on the order of about 1 inch.

In order to monitor, or sense, the internal pressure in bottle 10, a pressure transducer (PT) is attached into the conduit 24. Associated with the pressure transducer is a suitable, conventional signal processor S.P.-1. The signal processor provides the needed voltage to excite, or operate, the pressure transducer and to amplify the electrical signal from the pressure transducer, which electrical signal is related to the internal pressure in the bottle, and which signal is transmitted to an X-Y flat bed recorder 40. A suitable pressure transducer is a Statham, PA-731TC-200-350. Additionally an electrical signal which is related to the movement, or position, of the piston is generated and transmitted to recorder 40. Hence it will be seen that the flat bed recorder 40 then provides an automatic graphic presentation in which the Y-axis corresponds to pressure and the X-axis corresponds to the movement, or position, of the piston. As generally indicated above the linear movement of the piston is related to the volume of water displaced which in turn is related to the volumetric distortion of bottle 10. Hence the plot produced by recorder 40 is in essence a stress-strain curve for the thermoplastic bottle 10. In order to obtain the signal for developing the X-axis of the plot by recorder 40 there is employed a linear slide potentiometer P, for example a Bourns 14 inch (stroke) 7 K-ohm BO-24-2000-1285-002 linear potentiometer. Potentiometer P includes a slide member 42. Piston rod 24 includes a plate 44 which is movable in unison therewith, for example as by being attached thereto by means of a collar and pin assembly generally designated 46. Slide 42 of potentiometer P is mechanically coupled to plate 44, to allow direct monitoring of the rod movements, by any suitable means such as for example by a pin attachment 48. Thus, as will be seen, as the servomotor 28 causes drive screw 38 to move piston rod 24 upwardly the slide plate 44 moves in unison with piston rod 24 and similarly causes slide 42 of potentiometer P to move in unison therewith because of the mechanical coupling. A stable reference voltage is applied across this potentiometer and, as the piston is moved, and its position changed, a variable voltage output in direct relation to such position, or movement, is obtained from the potentiometer. Associated with potentiometer P is a signal processor (SP-2) which includes appropriate conventional circuitry to provide said reference voltage, and includes suitable circuitry to render the piston-position related signal compatible with the input of recorder 40 so as to prevent any unfavorable electrical interaction.

Thus it will be seen that the result of the test is an automatic graphic presentation of a plot of pressure against piston displacement, or a stress-strain type curve, which is rapidly, accurately, and reliably produced in a simple fashion and in a short period of time. The invaluable nature of such a curve will be readily apparent to those skilled in the art. For example the initial (linear) slope of the curve i.e. the elastic region, provides information as to the stiffness of the bottle and its resistance to deformation. The elastic yield point, i.e., the point at which the upper portion of the curve begins to deviate from linearity is a measure of the bottle strength, which in turn is related to how well, for example, a biaxially oriented thermoplastic bottle has been oriented. The 50 psi pressure point on the curve is an indication of the bottle expansion which will occur when a bottle is filled with a carbonated beverage, capped, and brought to room temperature. The overall shape of the curve is ideally suited for quality control purposes as a comparison of how the functionality, for example, strength and quality, of one bottle compares with another.

While the present invention has been described with particularity it will, of course, be apparent that modification is possible which pursuant to the patent statutes and laws do not depart from the spirit and scope thereof.

We claim:

1. A method for producing a stress-strain type curve for evaluating the functionality of a thermoplastic bottle comprising:
   internally pressurizing a thermoplastic bottle with an incompressible fluid by relative movement of a piston and a cylinder,
   sensing the pressure of said fluid and sensing the relative movement of said piston and cylinder as said bottle is being pressurized by such movement,
   graphically recording said sensed pressure and said sensed relative movement as said bottle is being pressurized.

2. The method of claim 1 wherein said bottle is a biaxially oriented bottle.

3. The method of claim 1 wherein the relative movement of said piston is sensed by the movement of the slide of a slide potentiometer and a pressure transducer senses the pressure.

4. A sensitive, automatic method for testing the functionality of a thermoplastic bottle comprising:
   providing a thermoplastic bottle and a piston-cylinder assembly,
   establishing a filled, sealed fluid communication of an incompressible fluid between said assembly and the interior of said bottle,
   driving the piston rod of said piston so as to increase the internal pressure of said fluid in said bottle,
   transmitting an electrical signal which is related to the internal pressure in said bottle to a recorder, and driving a slide of a slide potentiometer as said rod is driven and transmitting an electrical signal which is related to movement of said piston to a recorder;
   automatically plotting said respective electrical signals with said recorder so as to provide a graph in which one axis corresponds to pressure and another axis corresponds to the piston movement.

5. An apparatus for testing the functionality of a thermoplastic bottle comprising:
   a piston and cylinder assembly in sealed fluid communication with said bottle,
   means for driving said piston so as to increase the internal pressure of said fluid in said bottle,
   means responsive to the movement of said piston for generating a piston position related electrical signal,
   means for providing a bottle-pressure related electrical signal and,
   means operatively receiving said signals and graphically presenting said signals in the form of a graph in which one axis is pressure related and another axis is related to the piston position.

6. The apparatus of claim 5 wherein said means responsive to piston movement comprises a potentiometer having a voltage output which varies with the movement of said piston.

7. The improvement of claim 6 wherein said potentiometer is a slide potentiometer.

8. The improvement of claim 7 wherein the slide of said potentiometer is coupled to said piston for movement therewith.

* * * * *